US006103793A

United States Patent [19]

[11] Patent Number: 6,103,793
[45] Date of Patent: Aug. 15, 2000

Osmond

[54] COMPOSITION AND PROCESS FOR RETARDING DRIFT AND PROMOTING DEPOSITION IN A SPRAYING OPERATION

[75] Inventor: Charles A. Osmond, Lostant, Ill.

[73] Assignee: Davidon, Inc., Unadilla, Ga.

[21] Appl. No.: 09/052,231

[22] Filed: Mar. 31, 1998

Related U.S. Application Data

[60] Provisional application No. 60/042,898, Mar. 31, 1997.

[51] Int. Cl.$^7$ .................................................. C08J 11/00

[52] U.S. Cl. .................................................. 524/80

[58] Field of Search .................................................. 524/80

[56] References Cited

U.S. PATENT DOCUMENTS

| | | | |
|---|---|---|---|
| 3,360,356 | 12/1967 | Vartiak | 524/389 |
| 3,413,109 | 11/1968 | Vartiak | 524/389 |
| 3,628,942 | 12/1971 | Vartiak | 524/389 |
| 4,413,087 | 11/1983 | Bernot | 524/389 |

OTHER PUBLICATIONS

Product Data Sheet from Nalco Chemical Company; Nalco–Trol Precision Spray Adjuvant; 1984.

Product Data Sheet from Nalco Chemical Company; Nalco–Trol II Precision Spray Adjuvant; 1984.

Product Data Sheet from Nalco Chemical Company; STA–PUT Deposition Aid; 1984.

Product Data Sheet from Nalco Chemical Company; Nalquatic Aquatic Herbicide Adjuvant; 1984.

Product Data Brochure from Nalco Chemical Company; Questions and Answers–STA–PUT Deposition Aid; 1985.

*Primary Examiner*—Terressa M. Boykin
*Attorney, Agent, or Firm*—Kennedy, Davis & Hodge, LLP

[57] ABSTRACT

A composition and process for retarding drift and promoting deposition of a treatment product in an agriculturally-related spraying operation, wherein the composition consists essentially of a mixture of (A) principal functioning agents comprising a polyvinyl polymer, a sulfonated lignin material and a synthetic latex material and (B) inert agents comprising water, a non-ionic surfactant, a viscosity modifier, a stabilizer and a low odor paraffin solvent.

18 Claims, No Drawings

COMPOSITION AND PROCESS FOR RETARDING DRIFT AND PROMOTING DEPOSITION IN A SPRAYING OPERATION

This application claims the benefit of U.S. Provisional Application Ser. No. 60/042,898, filed Mar. 31, 1997.

TECHNICAL FIELD

This invention relates to a composition useful in a spraying operation. In a more specific aspect, this invention relates to a composition for retarding drift and promoting deposition of a treatment product in an agriculturally-related spraying operation.

This invention also relates to a process for retarding drift and promoting deposition of a treatment product in a spraying operation.

BACKGROUND OF THE INVENTION

In the agricultural industry, there are many situations in which pests must be controlled or eliminated to enhance and/or promote growth in a target area. The term "pests" is intended to be a broad term which includes small animals (such as field mice), weeds, insects, foliage, vegetation, etc. The term "target area" is used broadly in this application and is intended to include fields of crops such as corn or cotton, wooded areas, grazing areas for cattle, etc.

In combating pests in a target area, a product must be selected which is effective in controlling or eliminating the specific pest and which is usable in the particular target area. This product is also referred to as a "treatment product". Consideration of the target area involves factors such as terrain, wind conditions, temperature, humidity, density of the pest, etc.

A spraying operation is generally conducted by one of two methods-either the treatment product is sprayed into the target area from the air (i.e., by aerial application) or from the ground (i.e., by ground application). In some situations, an aerial application is used to more quickly cover a larger target area. Conventional equipment is available for either type of application.

The aerial and ground types of application share at least two objectives for best results: (a) to decrease or retard the amount of drift of the treatment product from the target area and (b) to increase or promote the amount of deposition of the treatment product within the target area. The term "drift" will be understood to refer to the tendency of a treatment product to travel out of the target area—i.e., miss the specific pest within the target area. The term "deposition" will be understood to refer to the amount of treatment product which contacts the pest within the target area.

The problems of drift and deposition of the treatment product are encountered by people in agriculturally-related situations, whether farmers working with crops, people working with forests, etc.

Several materials and methods halve been developed in an effort to retard drift and promote deposition in spraying operations. Reference is made to the disclosures of Vartiak U.S. Pat. No. 3,360,356; Vartiak U.S. Pat. No. 3,413,109; Vartiak U.S. Pat. No. 3,628,942; and Bernot U.S. Pat. No. 4,413,087.

However, for various reasons, there continues to be a need in the agricultural industry for a composition and process by which spray drift can be decreased or retarded and by which spray deposition can be increased or promoted.

SUMMARY OF THE INVENTION

Briefly described, the present invention provides a composition which is a mixture of principal functioning agents (a polyvinyl polymer, a sulfonated lignin material and a synthetic latex material) and inert agents. The term "principal functioning agents" will be understood to refer to the active ingredients of this composition, and the term "inert agents" will be understood to refer to the inactive ingredients of this composition.

The present invention provides a composition which can be effectively used to retard drift and promote deposition of a treatment product in an agriculturally-related spraying operation.

In addition, the present invention provides a process for retarding drift and promoting deposition in an agriculturally-related spraying operation, wherein a treatment product is combined or mixed with the novel composition of the present invention.

Accordingly, an object of this invention is to provide a composition to retard drift of a treatment product in a spraying operation.

Another object of this invention is to provide a composition to promote deposition of a treatment product in a spraying operation.

Another object of this invention is to provide a composition to retard drift of a treatment product in an agriculturally-related spraying operation.

Another object of this invention is to provide a composition to promote deposition of a treatment product in a an agriculturally-related spraying operation.

Another object of this invention is to provide a process for retarding drift of a treatment product in a spraying operation.

Still another object of this invention is to provide a process for promoting deposition of a treatment product in a spraying operation.

Still another object of this invention is to provide a process for retarding drift of a treatment product in an agriculturally-related spraying operation.

Still another object of this invention is to provide a process for promoting deposition of a treatment product in an agriculturally-related spraying operation.

Still another object of this invention is to provide a composition which, when mixed with a treatment product and sprayed into a target area, provides a spray having fewer fine droplets (i.e., less than 114 microns) and a narrower range of droplet sizes.

These and other objects, features and advantages of this invention will become apparent from the following detailed description.

DETAILED DESCRIPTION OF THE INVENTION

The present invention provides a composition consisting essentially of a mixture of;

from about 5.2 to about 7.5 percent by weight of principal functioning agents comprising a polyvinyl polymer; a sulfonated lignin material; and a synthetic latex material; and from about 92.5 to about 94.8 percent by weight of inert agents comprising water; a non-ionic surfactant; a viscosity modifier; a stabilizer; and a low odor paraffin solvent;

wherein the composition retards drift and promotes deposition of a treatment product in an agriculturally-related spraying operation.

In addition, the present invention provides a process for retarding drift and promoting deposition of a treatment product in an agriculturally-related spraying operation, wherein the process comprises the steps of:

obtaining an effective amount of a treatment product;

combining the treatment product with a composition consisting essentially of a mixture of from about 5.2 to about 7.5 percent by weight of principal functioning agents comprising a polyvinyl polymer; a sulfonated lignin material; and a synthetic latex material; and from about 92.5 to about 94.8 percent by weight of inert agents comprising water; a non-ionic surfactant; a viscosity modifier; a stabilizer; and a low odor paraffin solvent; and spraying the combination into a target area.

The treatment product used in this invention can be a conventional pesticide, herbicide, defoliant, miticide, fungicide, insecticide or other product designed to control or eliminate a particular pest within the target area. The amount of treatment product will depend upon the objectives of the spraying operation.

As noted earlier in this application, the spraying operation can be conducted from the air or from the ground.

The novel composition of this invention consists essentially of principal functioning agents comprising a polyvinyl polymer, a sulfonated lignin material and a synthetic latex material.

Polyvinyl polymers are well known in the industry, and many such polymers can be used as a principal functioning agent in the composition of the present invention. The specific polyvinyl polymer will depend upon various factors associated with the spraying operation, such as the specific pest, size of the target area, wind and temperature conditions, etc. Suitable polyvinyl polymers include those sold under the trademarks NALCO-625 and NALCO-2332 by Nalco Chemical Company (Naperville, Ill.).

A preferred polyvinyl polymer is commercially available in an emulsion form from Nalco Chemical Company under the trademark NALCOTROL. The emulsion form preferably contains a viscosity modifier (such as sodium sulfate) to provide a more manageable viscosity and a stabilizer (such as isopropyl alcohol) to enhance shelf stability.

In a preferred embodiment of this invention, the polyvinyl polymer in emulsion form is inverted to a solution form by the addition of water. This inversion provides a form which is easier to transport and otherwise handle.

The polyvinyl polymer contributes a "visco-elastic" effect by increasing the viscosity of the final spray product. This effect results in a shift of the droplet spectrum, so that there are fewer fine droplets (i.e., less than 114 microns) of the final spray product and a more narrow range of droplet sizes.

The sulfonated lignin material is preferably stabilized and is used to increase the specific gravity of the final spray product to enhance the settling of the spray droplets in the target area. The sulfonated lignin material is also known to have an effect in reducing the breakdown of some treatment products due to exposure to ultraviolet radiation. In this instance, the sulfonated lignin material is believed to act as a UV blocker for some treatment products.

Sulfonated lignin materials are well known in the industry, and many such materials can be used as a principal functioning agent in the composition of the present invention. As with the polyvinyl polymer, the specific sulfonated lignin material will depend upon various factors associated with the spraying operation, such as the specific pest, size of the target area, wind and temperature conditions, etc.

A preferred sulfonated lignin material in stabilized form is commercially available from Nalco Chemical Company under the trademark NALCO-8803.

The synthetic latex material is used to increase the weatherability (i.e., the resistance to wash off by rain) of the spray droplet on the specific pest within the target area. Synthetic latex materials are also well known in the industry, and many such materials can be used as a principal functioning agent in the composition of the present invention.

A preferred synthetic latex material is available commercially from Loveland Industries (Greeley, Colo.) under the trademark BOND. Other synthetic latex materials can be used, such as material sold under the trademark AC-33N by Rohm & Haas Co. (Philadelphia, Pa.).

The synthetic latex material must be selected with specific regard to molecular weight, viscosity and pH, and with specific regard to various factors associated with the spraying operation (such as the specific pest, size of the target area, wind and temperature conditions, etc.) Further, the synthetic latex material must be exempt from tolerance under the provisions of 40 C.F.R. § 180.1001(d).

In a preferred embodiment of this invention, sodium sulfate, isopropyl alcohol and the polyvinyl polymer in emulsion form are mixed with deionized water in a conventional tank, where the polyvinyl polymer inverts to a solution polymer. This mixture is then moved to a second tank and aged for 24–48 hours. After aging, the mixture is agitated for at least 30 minutes, after which tests are conducted in regard to specific gravity, viscosity, percent solids and activity.

Next, the mixture is moved to a third tank where the sulfonated lignin and synthetic latex materials are added, and the entire contents are mixed.

In mixing the principal functioning agents, the sequence and speed of addition of the sulfonated lignin and synthetic latex materials are critical to creating a stable composition. Preferably, a conventional blending tank is first filled with a predetermined amount of the polyvinyl polymer solution, and then the sulfonated lignin material is added slowly to the suction side of a conventional agitation pump at a rate not to exceed 0.5 gallon per minute. The mixture in the tank is then agitated until a homogeneous mixture is achieved. Next, the synthetic latex material is added to the suction side of the agitation pump at a rate not to exceed 0.25 gallon per minute until a homogeneous mixture is achieved.

The mixture can then be packaged into suitable containers, such as a 2.5 gallon jug, 110 gallon mini-bulk or shipped in bulk containers.

In general, the inert agents are water, a non-ionic surfactant, a viscosity modifier, a stabilizer and a low odor paraffin solvent (e.g., kerosene). Non-ionic surfactants and viscosity modifiers are well known in the industry. Preferred viscosity modifiers are sodium salts, such as sodium sulfate, sodium chloride, sodium citrate and sodium nitrate. Stabilizers and low odor paraffin solvents are also well known in the industry. A preferred low odor paraffin solvent is kerosene, and a preferred stabilizer in isopropyl alcohol.

Upon being used with a treatment product in a spraying operation, the quantity of driftable fine droplets is greatly reduced (as compared to the same spraying process but without the composition of this invention), which results in up to 30 percent more treatment product contacting the specific pest.

In general terms, the composition of this invention is comprised of from about 5.2 to about 7.5 percent by weight of the principal functioning agents and from about 92.5 to about 94.8 percent by weight of the inert agents. Preferred percentages are 5.2 and 94.8 for the principal functioning and inert agents, respectively.

With regard to the principal functioning as the following percentage ranges (by weight) are useful in this invention:

| | |
|---|---|
| Polyvinyl polymer solution | 88.0–92.0 |
| Sulfonated lignin material | 4.8–5.2 |
| Synthetic latex material | 4.8–5.2 |

In a preferred embodiment of this invention, the principal functioning agents are comprised of about 90 percent by weight polyvinyl polymer solution; about 5 percent by weight sulfonated lignin material; and about 5 percent by weight synthetic latex material.

This invention has been described in detail with particular reference to certain embodiments, but variations and modifications can be made without departing from the spirit and scope of the invention as defined in the following claims.

What is claimed is:

1. A composition consisting essentially of a mixture of:

A. from about 5.2 to about 7.5 percent by weight of principal functioning agents comprising a polyvinyl polymer; a sulfonated lignin material; and a synthetic latex material; and B. from about 92.5 to about 94.8 percent by weight of inert agents comprising water; a non-ionic surfactant; a viscosity modifier; a stabilizer; and a low odor paraffin solvent;

wherein the composition retards drift and promotes deposition of a treatment product in an agriculturally-related spraying operation.

2. A composition as defined by claim 1 wherein the principal functioning agents consist essentially of from 88.0–92.0 percent by weight of the polyvinyl polymer solution, from 4.8–5.2 percent by weight of the sulfonated lignin material and from 4.8–5.2 percent by weight of the synthetic latex material.

3. A composition as defined by claim 1 wherein the viscosity modifier is a sodium salt.

4. A composition as defined by claim 3 wherein the sodium salt is sodium sulfate, sodium chloride, sodium citrate or sodium nitrate.

5. A composition as defined by claim 3 wherein the sodium salt is sodium sulfate.

6. A composition as defined by claim 1 wherein the treatment product is a pesticide, herbicide, defoliant, miticide, fungicide or insecticide.

7. A composition as defined by claim 1 wherein the low odor paraffin solvent is kerosene.

8. A composition as defined by claim 1 wherein the mixture consists essentially of about 5.2 percent by weight of the principal functioning agents and about 94.8 percent by weight of the inert agents.

9. A process for retarding drift and promoting deposition of a treatment product in an agriculturally-related spraying operation, wherein the process comprises the steps of:

I. obtaining an effective amount of a treatment product;

II. combining the treatment product with a composition consisting essentially of a mixture of:

A. from about 5.2 to about 7.5 percent by weight of principal functioning agents comprising a polyvinyl polymer; a sulfonated lignin material; and a synthetic latex material; and B. from about 92.5 to about 94.8 percent by weight of inert agents comprising water; a non-ionic surfactant; a viscosity modifier; a stabilizer; and a low odor paraffin solvent;

III. spraying the combination into a target area.

10. A process as defined by claim 9 wherein the principal functioning agents consist essentially of from 88.0–92.0 percent by weight of the polyvinyl polymer solution, from 4.8–5.2 percent by weight of the sulfonated lignin material and from 4.8–5.2 percent by weight of the synthetic latex material.

11. A process as defined by claim 9 wherein the viscosity modifier is a sodium salt.

12. A process as defined by claim 11 wherein the sodium salt is sodium sulfate, sodium chloride, sodium citrate or sodium nitrate.

13. A process as defined by claim 11 wherein the sodium salt is sodium sulfate.

14. A process as defined by claim 9 wherein the treatment product is a pesticide, herbicide, defoliant, miticide, fungicide or insecticide.

15. A process as defined by claim 9 wherein the low odor paraffin solvent is kerosene.

16. A process as defined by claim 9 wherein the mixture comprises about 5.2 percent by weight of the principal functioning agents and from about 94.8 percent by weight of the inert agents.

17. A process as defined by claim 9 wherein the stabilizer is isopropyl alcohol.

18. A combination product which consists essentially of (a) a pesticide, herbicide, defoliant, miticide, fungicide or insecticide and (b) a process consisting essentially of from about 5.2 to about 7.5 percent by weight of principal functioning agents and from about 92.5 to about 94.8 of inert agents, wherein the principal functioning agents comprise a polyvinyl polymer, a sulfonated lignin material and a synthetic latex material and the inert agents comprise a non-ionic surfactant, a viscosity modifier and a low odor paraffin solvent.

* * * * *